US012653454B2

(12) United States Patent
Statan et al.

(10) Patent No.: US 12,653,454 B2
(45) Date of Patent: Jun. 16, 2026

(54) METHODS AND SYSTEMS FOR IMPROVING MEASUREMENT OF SLEEP DATA BY CLASSIFYING USERS BASED ON SLEEPER TYPE

(71) Applicant: Google LLC, Mountain View, CA (US)

(72) Inventors: Alexander Statan, Berkeley, CA (US); Sarah Ann Stokes Kernasovskiy, San Francisco, CA (US); Alexandros Antonios Pantelopoulos, El Cerrito, CA (US); Conor Joseph Heneghan, Campbell, CA (US)

(73) Assignee: GOOGLE LLC, Mountain View, CA (US)

( * ) Notice: Subject to any disclaimer, the term of this patent is extended or adjusted under 35 U.S.C. 154(b) by 543 days.

(21) Appl. No.: 18/013,738

(22) PCT Filed: Oct. 21, 2021

(86) PCT No.: PCT/US2021/056027
§ 371 (c)(1),
(2) Date: Dec. 29, 2022

(87) PCT Pub. No.: WO2023/069102
PCT Pub. Date: Apr. 27, 2023

(65) Prior Publication Data
US 2024/0090827 A1      Mar. 21, 2024

(51) Int. Cl.
*A61B 5/00* (2006.01)
*A61B 5/11* (2006.01)
(Continued)

(52) U.S. Cl.
CPC .......... *A61B 5/4809* (2013.01); *A61B 5/1126* (2013.01); *A61B 5/681* (2013.01);
(Continued)

(58) Field of Classification Search
CPC ... A61B 5/4809; A61B 5/4812; A61B 5/4806; A61B 5/4815; A61B 5/1118;
(Continued)

(56) References Cited

U.S. PATENT DOCUMENTS 11,717,188 B2      8/2023   Arnold et al.
2011/0230790 A1*   9/2011   Kozlov ................ G04G 13/026
                                                   600/595
(Continued)

FOREIGN PATENT DOCUMENTS

CN          106725382          5/2017
CN          113288095          8/2021
(Continued)

OTHER PUBLICATIONS

Machine translation of WO-2020085553 (2020).*
(Continued)

*Primary Examiner* — Manuel L Barbee
(74) *Attorney, Agent, or Firm* — DORITY & MANNING P.A.

(57) ABSTRACT

The present disclosure is directed towards systems and methods for improving analysis of sleep data by classifying users based on sleeper type. In particular, a wearable computing system can obtain a first set of motion sensor data from the motion sensor for a user during a first period. The wearable computing system can determine a sleeper type from a plurality of sleeper types for the user based on the first set of motion sensor data received from the motion sensor. The wearable computing system can select a sleep analysis model from a plurality of sleep analysis models based on the sleeper type determined for the user. The wearable computing system can use the selected sleep analysis model to analyze a second set of motion sensor data
(Continued)

from a second period to determine one or more sleep characteristics for the user during the second period.

16 Claims, 8 Drawing Sheets

(51) Int. Cl.
| | |
|---|---|
| *G01P 13/00* | (2006.01) |
| *G01P 15/18* | (2013.01) |
| *G06N 3/084* | (2023.01) |

(52) U.S. Cl.
CPC ............ *A61B 5/7267* (2013.01); *G01P 13/00* (2013.01); *G01P 15/18* (2013.01); *G06N 3/084* (2013.01); *A61B 5/4812* (2013.01); *A61B 2562/0219* (2013.01)

(58) Field of Classification Search
CPC ......... A61B 5/1126; A61B 5/11; A61B 5/681; A61B 5/7267; A61B 2562/0219; A61B 2560/0223; G01P 13/00; G01P 15/18; G06N 3/084; G16H 40/63; G16H 50/20; G16H 50/30
See application file for complete search history.

(56) References Cited

U.S. PATENT DOCUMENTS

| | | | |
|---|---|---|---|
| 2016/0279501 A1 | 9/2016 | Jang et al. | |
| 2019/0340515 A1 | 11/2019 | Pathak et al. | |
| 2022/0104758 A1 | 4/2022 | Thein et al. | |
| 2022/0240843 A1 * | 8/2022 | Kokoszka | G16H 50/70 |
| 2022/0265208 A1 * | 8/2022 | Heneghan | A61B 5/7267 |
| 2024/0090829 A1 * | 3/2024 | Gu | A61B 5/4815 |

FOREIGN PATENT DOCUMENTS

| | | | |
|---|---|---|---|
| EP | 3377963 | 9/2018 | |
| KR | 20210075313 | 6/2021 | |
| WO | WO 2016/097945 | 6/2016 | |
| WO | WO 2018/048951 | 3/2018 | |
| WO | WO-2020085553 A1 * | 4/2020 | A61B 5/00 |

OTHER PUBLICATIONS

International Preliminary Report on Patentability for Application No. PCT/US2021/056027, mailed May 2, 2024, 8 pages.
International Search Report for Application No. PCT/ US2021/ 056027, mailed on Jul. 22, 2022, 6 pages.
Chinese Search Report Corresponding to Application No. 2021800465810 on Jun. 18, 2025.

* cited by examiner

METHODS AND SYSTEMS FOR IMPROVING MEASUREMENT OF SLEEP DATA BY CLASSIFYING USERS BASED ON SLEEPER TYPE

CROSS-REFERENCE TO RELATED APPLICATIONS

The present application is based upon and claims the right of priority under 35 U.S.C. § 371 to International Application No. PCT/US2021/056027 filed on Oct. 21, 2021, which is incorporated by reference herein.

FIELD

The present disclosure relates generally to improving the accuracy of data analysis of data gathered by sensors in a wearable computing device. More particularly, the present disclosure relates to methods and systems for improving measurement of sleep data by classifying users based on sleeper type.

BACKGROUND

Recent advances in wearable technology such as fitness trackers and smart watches have enabled the collection of data from a user based on sensors included in the wearable computing devices. One use of the data collected can be the analysis of the sleep patterns of a user. For example, using data gathered by a motion sensor such as an accelerometer, a wearable computing device can estimate the amount and quality of sleep for a user during a particular sleep session. However, users' sleep patterns and behavior can vary such that the systems and tools that accurately determine sleep data for some types of users may be inaccurate when used to analyze the sleep data generated by another type of user.

SUMMARY

Aspects and advantages of embodiments of the present disclosure will be set forth in part in the following description, or may be learned from the description, or may be learned through practice of the embodiments.

One example embodiment includes a wearable computing device. The wearable computing device includes a motion sensor configured to generate motion sensor data based on movements of a user. The wearable computing device includes one or more processors that execute computer-readable instructions to obtain a first set of motion sensor data from the motion sensor for the user during a first period. The one or more processors can further execute computer-readable instructions to determine a sleeper type from a plurality of sleeper types for the user based on the first set of motion sensor data received from the motion sensor. The one or more processors can further execute computer-readable instructions to select a sleep analysis model from a plurality of sleep analysis models based on the sleeper type determined for the user. The one or more processors can further execute computer-readable instructions to use the selected sleep analysis model to analyze a second set of motion sensor data from a second period to determine one or more sleep characteristics for the user during the second period.

Another example embodiment can include a computer-implemented method that comprises obtaining, by a computing device including one or more processors, a first set of motion sensor data from the motion sensor for a user during a first period. The method further comprises determining, by the computing device, a sleeper type from a plurality of sleeper types for the user based on the first set of motion sensor data received from the motion sensor. The method further comprises selecting, by the computing device, a sleep analysis model from a plurality of sleep analysis models based on the sleeper type determined for the user. The method further comprises using, by the computing device, the selected sleep analysis model to analyze a second set of motion sensor data from a second period to determine one or more sleep characteristics for the user during the second period.

Another example embodiment can be a non-transitory computer readable storage medium having computer-readable program instructions embodied thereon that, when executed by one or more processors, cause the one or more processors to obtain a first set of motion sensor data from the motion sensor for a user during a first period. The instructions can further cause the one or more processors to determine a sleeper type from a plurality of sleeper types for the user based on the first set of motion sensor data received from the motion sensor. The instructions can further cause the one or more processors to select a sleep analysis model from a plurality of sleep analysis models based on the sleeper type determined for the user. The instructions can further cause the one or more processors to use the selected sleep analysis model to analyze a second set of motion sensor data from a second period to determine one or more sleep characteristics for the user during the second period.

Other example aspects of the present disclosure are directed to systems, apparatus, computer program products (such as tangible, non-transitory computer-readable media but also such as software which is downloadable over a communications network without necessarily being stored in non-transitory form), user interfaces, memory devices, and electronic devices for determining a user's sleeper type.

These and other features, aspects and advantages of various embodiments will become better understood with reference to the following description and appended claims. The accompanying drawings, which are incorporated in and constitute a part of this specification, illustrate embodiments of the present disclosure and, together with the description, serve to explain the related principles.

BRIEF DESCRIPTION OF THE DRAWINGS

A detailed discussion of embodiments directed to one of ordinary skill in the art are set forth in the specification, which refers to the appended figures, in which.

DETAILED DESCRIPTION

Figure 1:
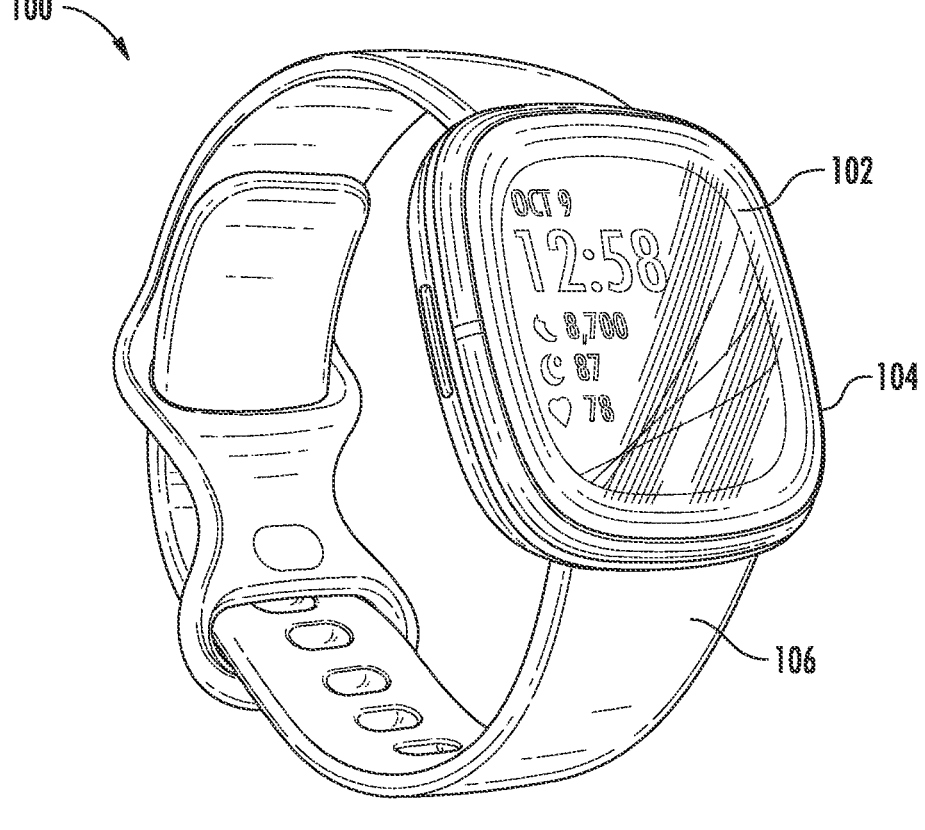
FIG. 1 illustrates an example wearable computing device in accordance with example embodiments of the present disclosure.

Reference now will be made in detail to embodiments, one or more examples of which are illustrated in the drawings. Each example is provided by way of explanation of the embodiments, not limitation of the present disclosure. In fact, it will be apparent to those skilled in the art that various modifications and variations can be made to the embodiments without departing from the scope or spirit of the present disclosure. For instance, features illustrated or described as part of one embodiment can be used with another embodiment to yield a still further embodiment. Thus, it is intended that aspects of the present disclosure cover such modifications and variations.

Example aspects of the present disclosure are directed towards a system for improving the classification of sleep data by determining a user's sleeper type and selecting a sleep analysis model for interpreting sleep data (e.g., motion sensor data) more accurately based on the user's sleeper type. For example, some users move significantly more during sleep (e.g., high-movement or twitchy sleepers) than is typically expected for other users. As a result, sleep data produced by sleep analysis models can be inaccurate for such high-movement users. Therefore, to improve accuracy, a user classification system can determine a user's sleeper type and select a sleep analysis model that has been trained or otherwise designed to accurately determine sleep characteristics (e.g., information about a user's sleep session or sleep habits) for the user's specific sleeper type.

A wearable computing device can include a motion sensor (e.g., an accelerometer) that detects the movement of a user wearing the wearable computing device. The wearable computing device can collect motion sensor data from a user over one or more sleep sessions. Based on this data (e.g., past sleep sessions), the computing device can determine a sleeper type of the user. For example, the computing device can determine the average amount of time between detected movements for a user during a sleep session. If the average amount of time between movements is below a threshold, the user can be determined to have a high-movement sleeper type (e.g., a twitchy sleeper type). Once a sleeper type is determined for a particular user, the user classification system can select a particular sleep analysis model from a plurality of sleep analysis models for use when analyzing future sleep data received from that user.

For example, a user may wear a wearable computing device (e.g., a fitness band) to detect, among other things, metrics that can represent information about the amount and quality of sleep that the user experiences. In order to accurately determine one or more sleep characteristics based on the sensor data produced by the wearable computing device, a user classification system (e.g., included in the wearable computing device itself or at a remote computing system) can use past sleep data to determine a sleeper type for the user. For example, the user classification system can determine a sleeper type for a user based on one or more sleep factors. The one or more sleep factors can be determined based on sleep data collected previously from the user. In some examples, the one or more sleep factors can include the average amount of time between movements, the minimum or average number of times a user moves within any 100-minute period of the sleep session, and/or other indications of an amount, frequency, and/or duration of movement during sleep.

The user classification system can compare the one or more sleep factors to one or more high-movement thresholds. If the one or more sleep factors exceed the threshold(s), the user classification system can determine that the sleeper type for the user is a high-movement sleeper type. In response, the user classification system can select a sleep analysis model or another analysis tool that has been configured for a high-movement sleeper type user.

Once a sleep analysis model has been selected, the user classification system can obtain further motion sensor data for the user and determine sleep characteristic data using the further motion sensor data as input to the selected sleep analysis model. For example, the user classification system can determine one or more sleep characteristics that describe a user's sleep session at the time that the further motion sensor data was obtained including whether the user is asleep, a current sleep state of the user, whether the user has transitioned between sleep states, and if so, when those transitions occurred.

More specifically, a wearable computing device can include any computing device that is integrated into an object that is meant to be worn by a user. For example, wearable computing devices can include, but are not limited to, smartwatches, fitness bands, computing devices integrated into jewelry such as smart rings or smart necklaces, computing devices integrated into items of clothing such as jackets, shoes, and pants, and wearable glasses with computing elements included therein. In some examples, a wearable computing device can include one or more sensors intended to gather information with the permission of the user that is wearing the wearable computing device.

In some examples, the wearable computing device can include one or more motion sensors. Motion sensors can include an accelerometer that can measure the movement of a user along three axes (e.g., x, y, and z dimensions). In some examples, the wearable computing device can transmit the motion sensor data to a server system for analysis. In other examples, the analysis can be performed by the wearable computing device. Thus, the user classification system can be enabled or executed at one or more of the wearable computing device, a remote server system, or another computing system that can perform analysis of the motion sensor data and communicate with the wearable computing device to receive the motion sensor data.

A user classification system included in the computing system (e.g., either the remote server system or the wearable computing device) can determine for a particular period (e.g., a 30-second interval), the range of movement from a user in each of the three dimensions. The range of movement for a particular interval can be used to determine a sleep coefficient. The range can be determined by determining a minimum value for each axis and a maximum value for each axis during the particular period and subtracting the minimum value from the maximum value.

The sleep coefficient can be determined based on the movement of the user during the time interval. For example, the sleep coefficient can be generated by summing the range of movement for all three axes. In another example, the sleep coefficient can be set to the maximum range of movement among all three axes. In yet other examples, the sleep coefficient can be set to the average range of movement for all three axes.

In some examples, other sensors can be used to detect the motion of the user. For example, an infra-red sensor can be used to sense the motion of a user. In addition, other factors, such as a user's breathing can be measured by an infra-red sensor and can be used to estimate the user's movement and otherwise determine sleep data for a user. Similarly, a step counter can be used to determine a user's sleep state (e.g., a walking user is generally not sleeping). In some examples, sensors can measure the heartbeat of a user and use that data to determine the motion of a user. Similarly, a sensor included in a wearable computing device can be used to perform photoplethysmography (PPG). The PPG data can be used to determine the motion of the user.

Based on the sleep coefficient, a user classification system can determine whether the respective interval includes user movement or not. In some examples, the user classification system can determine the amount of movement of a user during a period that includes several intervals. For example, if each interval is 30 seconds long, the user classification system can determine whether a user is asleep for a 10-minute period based on the plurality of intervals included in that period. In some examples, if the amount of movement exceeds a certain threshold, the user classification system can determine that the user is not asleep.

In some examples, the sleep coefficient for a given time interval can be sorted into one of a plurality of categories or bin, with each bin representing a predetermined range of the sleep coefficient value. Each bin can be associated with a particular determination about the user. Thus, the smallest bin can be associated with no movement during the interval and can be associated with sleep with a high degree of confidence. Similarly, a sleep coefficient above a certain level can be categorized The user classification system can generate a time series of motion sensor data representing a plurality of sequential intervals, with each interval being classified as including movement or not including movement. The time series of motion sensor data representing a plurality of sequential intervals can be referred to as a sleep log. The user classification system can determine the sleeper type of a user based on the time series of motion sensor data. Thus, to determine a user's sleeper type, the user classification system can obtain the motion sensor data for a sleep session. The user classification system can determine one or more factors based on the motion sensor data for the sleep session. The factors can include an average amount of time between movements during the sleep session, the minimum or average sleep coefficient in any 100-minute period during the sleep session, and/or other indications of the amount, frequency, or duration of movement during sleep.

Based on the one or more sleep factors (e.g., a minimum number of movements in a period and the average amount of time between movements), the user classification system can determine a sleeper type for the user. For example, if the number of times that a user moves during a period of sleep exceeds a particular threshold, the user classification system can determine that the sleeper type of the user is a high-movement sleeper type (e.g., a twitchy sleeper type). Other potential sleeper types can be associated with sleep disorders (e.g., insomnia), can be based on a user's sleep habits (e.g., a user who has several shorter sleep sessions rather than one long one), and so on.

Once a sleeper type is determined for a user, the user classification system can select a particular sleep analysis model for use when analyzing the sleep data of the user. For example, the user classification system can include a plurality of different computer-learned models, where each model has been trained based on data from or associated with a particular sleeper type. Thus, when the sleeper type of a user is determined, the user classification system can select a sleep analysis model that has been trained to more accurately analyze the motion sensor data or other sleep data produced by a user with that sleeper type.

In other examples, a single sleep analysis model is used but the specific parameter values associated with the model can be adjusted based on the sleeper type of a user. Thus, when a user sleeper type is determined, the user classification system can select the particular parameters associated with the sleeper type and use those parameters during the analysis of sleep data associated with the user.

In addition or alternatively, in some examples, the sleep analysis model can include (or use as a post-processing system) one or more rule-based classification steps that can perform additional analysis of the sleep characteristic data determined by the sleep analysis model in one or more specific situations. In some examples, the rule-based classification steps can be altered based on the sleeper type of the user (e.g., such that they produce different sleep characteristics for users of a first sleeper type and users of a second sleeper type.) In this way, the user classification system can select the most appropriate tools to analyze the motion sensor data of the user based on the user's sleeper type.

Using motion sensor data detected from a user during a second period as input to the sleep analysis model (e.g., different from the data for the first period that was used to determine the sleeper type of the user), the user classification system can determine one or more sleep characteristics for the second period. In some examples, the user classification system can determine whether the user was asleep for one or more portions of the second period. If so, the user classification system can determine when the sleep session began and when it ended. In addition, the user classification system can determine a current sleep state for the user. Sleep states can include an REM sleep state, a light sleep state, and a deep sleep state. In some examples, other sleep characteristics can be determined based on the sleep analysis model. For example, the sleep analysis model can generate a sleep score or other data representing the overall quality of the sleep session (e.g., based on a length of the sleep session and the time spent in each sleep state). Additional parameters that are not specifically related to sleep can use the data from the sleep analysis model as one factor used in their analysis such as a stress score and/or a fitness readiness score.

Embodiments of the disclosed technology provide a number of technical effects and benefits, particularly in the areas of user computing devices. In particular, embodiments of the disclosed technology provide improved techniques for analyzing sensor data associated with a sleeping user. For example, utilizing embodiments of the disclosed technology, a computing system can determine a sleeper type for a user and based on the sleeper type, select a sleep analysis model to use when analyzing the motion sensor data generated by a wearable computing device worn by a user. Customizing the sleep analysis model used to evaluate data for a specific user can increase the accuracy of sleep characteristics generated by the computing system and can result in a better and more useful user experience. Furthermore, this effect is accomplished with relatively little cost. As such, the disclosed embodiments enable additional functionality without significantly increasing the total cost of a wearable device.

With reference now to the figures, example aspects of the present disclosure will be discussed in greater detail.

FIG. 1 depicts the front view of an example wearable computing device 100 according to example embodiments of the present disclosure. In one embodiment, the wearable computing device 100 may be a wristband, a bracelet, a wristwatch, an armband, a ring placed around a digit of the user, or other wearable products that may be equipped with sensors as described in the present disclosure. In an example embodiment, the wearable computing device 100 is configured with a display 102, a device housing 104, a band 106, and one or more sensors. In an embodiment, the display 102 can be configured to present to a user data relating to the user's skin temperature, heart rate, sleep state, electroencephalogram, electrocardiogram, electromyography, electrooculogram, and other physiological data of the user (e.g., blood oxygen level). The display 102 can also be configured to convey data from additional ambient sensors contained within the wearable computing device 100. Example information conveyed on the display 102 from these additional ambient sensors can include a positioning, altitude, and weather of a location associated with the user. The display 102 can also convey data regarding the motion of the user (e.g., whether the user is stationary, walking, and/or running).

In an example embodiment, the display 102 can be configured to receive data input by the user. In an embodiment, a user can, by input on the display, request that the wearable computing device 100 generate additional data for display to the user (e.g., sleep data). In response, the display can present instructions to the user (e.g., instructions to place one or more fingers on sensor 210) to obtain the data requested. Furthermore, if, while the additional data is being gathered, the wearable computing device 100 determines that additional data is necessary, the display 102 can display instructions to the user (e.g., display "please continue to hold your finger against the sensor for 10 seconds").

In an example embodiment, the device housing 104 can be configured to contain one or more sensors described in the present disclosure. Example sensors contained by the device housing 104 can include motion sensors (e.g., accelerometer), a pulse oximeter, an IR motion sensor, skin temperature sensors, internal device temperature sensors, location sensors (e.g., GPS), altitude sensors, heart rate sensors, audio sensors, pressure sensors, gyroscopes, environmental sensors (e.g., bedside ultrasounds sensors), and other physiological sensors (e.g., blood oxygen level sensors). In an embodiment, the device housing 104 can also be configured to include one or more processors. The band 106 can be configured to secure the wearable computing device 100 around an arm of the user by, for example, connecting ends of the band 106 with a buckle, clasp, or another similar securing device, thereby allowing the wearable computing device 100 to be worn by the user.

Figure 2:
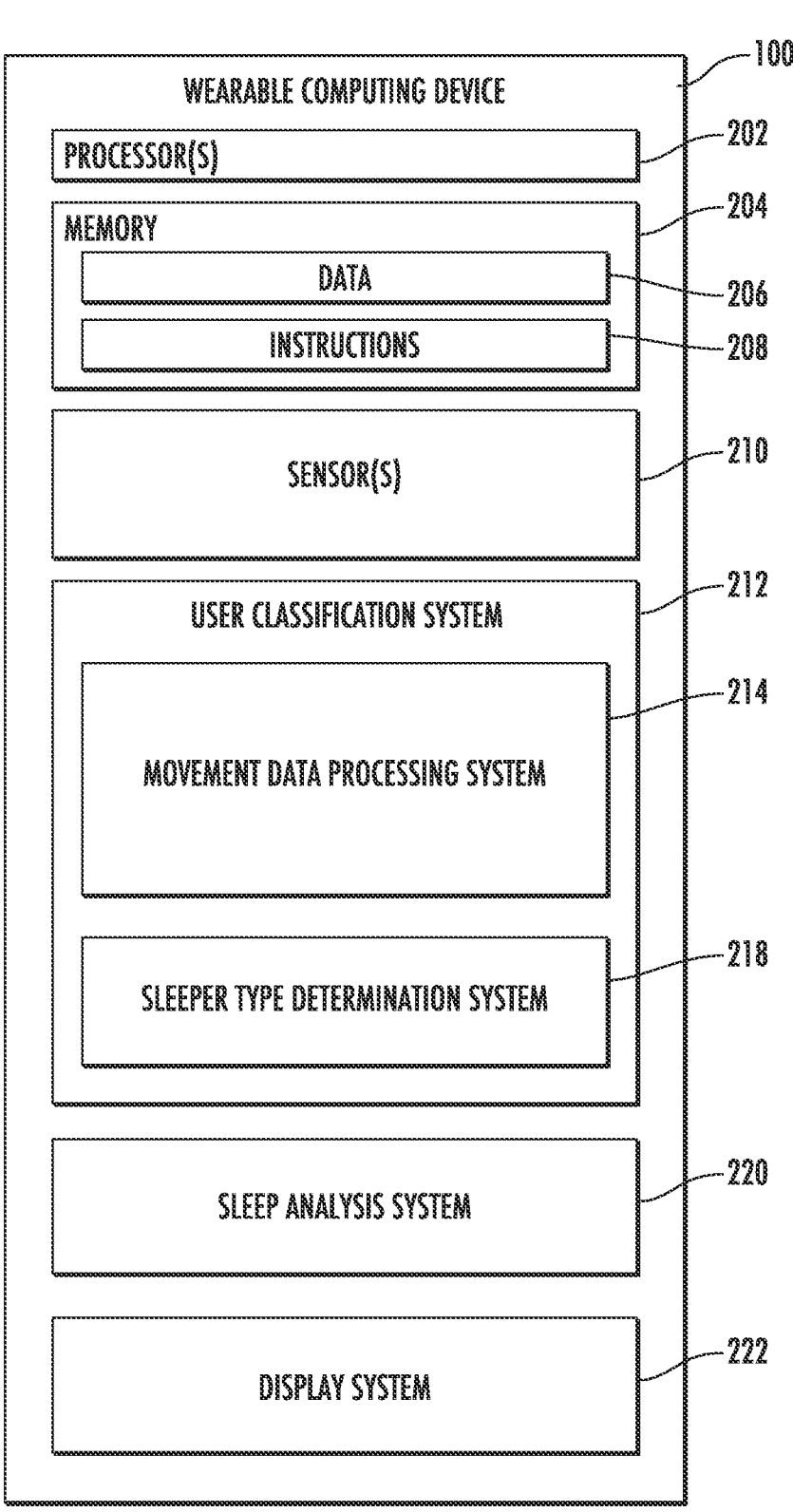
FIG. 2 illustrates a block diagram of an example computing environment that includes a wearable computing device having a sensor in accordance with example embodiments of the present disclosure.

FIG. 2 illustrates an example computing environment including a wearable computing device 100 in accordance with example embodiments of the present disclosure. In this example, the wearable computing device 100 can include one or more processors 202, memory 204, one or more sensors 210, a user classification system 212, a sleep analysis system 220, and a display system 222.

In more detail, the one or more processors 202 can be any suitable processing device that can be embedded in the form factor of a wearable computing device 100. For example, such a processor 202 can include one or more of: one or more processor cores, a microprocessor, an application-specific integrated circuit (ASIC), a FPGA, a controller, a microcontroller, etc. The one or more processors 202 can be one processor or a plurality of processors that are operatively connected. The memory 204 can include one or more non-transitory computer-readable storage mediums, such as RAM, ROM, EEPROM, EPROM, flash memory devices, etc., and combinations thereof.

In particular, in some devices, memory 204 can store instructions for implementing the user classification system 212, the sleep analysis system 220, and/or the display system 222. Thus, the wearable computing device 100 can implement the user classification system 212, the sleep analysis system 220, or the display system 222 to execute aspects of the present disclosure.

It will be appreciated that the term "system" can refer to specialized hardware, computer logic that executes on a more general processor, or some combination thereof. Thus, a system can be implemented in hardware, application specific circuits, firmware, and/or software controlling a general-purpose processor. In one embodiment, the system can be implemented as program code files stored on the storage device, loaded into memory, and executed by a processor or can be provided from computer program products, such as computer-executable instructions, that are stored in a tangible computer-readable storage medium such as RAM, hard disk or optical or magnetic media.

Memory 204 can also include data 206 and instructions 208 that can be retrieved, manipulated, created, or stored by the one or more processor(s) 202. In some example embodiments, such data can be accessed and used as input to the user classification system 212, the sleep analysis system 220, and/or the display system 222. In some examples, the memory 204 can include data used to perform one or more processes and instructions that describe how those processes can be performed.

In some examples, the wearable computing device 100 can include one or more sensors 210. For example, the sensors 210 can include, but are not limited to, one or more of: motions sensors (e.g., accelerometer), a pulse oximeter, an IR motion sensor, skin temperature sensors, internal device temperature sensors, location sensors (e.g., GPS), altitude sensors, heart rate sensors, audio sensors, pressure sensors, and other physiological sensors (e.g., blood oxygen level sensors).

In some examples, the one or more sensors 210 can detect movement of a user and provide motion data representing the movement to the wearable computing device 100. For example, an accelerometer can measure the movement of a user across three axes. For example, the accelerometer can measure the X, Y, and Z axes. Thus, as a user moves the accelerometer can generate data representing the movement and provide it to the wearable computing device 100. Other sensors, such as an IR laser sensor, a heartbeat sensor, a pulse oximeter, and so on can be used to determine the movement or activity level of a user.

The motion data generated by the sensors 210 can be transmitted to the user classification system 212. The user classification system 212 can use recorded motion data to estimate the sleeper type of the user. For example, the recorded motion data can be longitudinal data that was previously recorded from the user and was determined to be associated with a sleep session of the user. Specifically, a motion data processing system 214 can use the motion data to generate a sleep coefficient for a particular period. In some examples, the particular period can be a 30-second window of time. Other time increments can be used. The motion data processing system 214 can, based on motion data generated by the one or more sensors 210, determine an amount of movement in a respective time interval.

For example, the motion data processing system 214 can calculate the total movement in each of the axes that occur during the respective time interval. The sleep coefficient can represent the sum of movement in all three axes during the respective time interval. For example, the motion data processing system 214 can determine a minimum value and a maximum value for each axis during the respective time interval. The total range of movement along each of the axes can be determined by subtracting the minimum value for the axis from the maximum value for the axis.

Thus, the motion data processing system 214 can determine a total range of movement for that user during that increment of time. In some examples, the total range for each axis can be summed to generate the sleep coefficient. Alternatively or additionally, the sleep coefficient can be the average of the total range of movement detected for all three axes. In yet another example, the sleep coefficient can be set to the highest range value from the three different range values for the three axes. Additionally, or alternatively, the sleep coefficient can also be based, at least in part, on data other than the total range of movement. For example, the one or more sensors can provide data that describes whether the wearable computing device is currently being worn by the user (e.g., whether the fitness band is currently on the wrist of a user). In addition, the one or more sensors can determine the number of steps taken by the user during the time interval. These additional data inputs can be used to generate or update the motion coefficient for a particular time interval.

Once the sleep coefficient has been determined for a respective interval, the motion data processing system 214 can classify that particular interval as including movement or not including movement. In some examples, the sleep coefficient can be sorted into one of a plurality of sleep coefficient value bins, each bin representing a range of sleep coefficient values and being associated with a particular amount of movement. Thus, similar sleep coefficient values can be grouped together and movement can be determined based on rules determined for each bin.

Grouping or characterizing sleep coefficients into bins can reduce the amount of processing time and power needed to generate sleep factor information without a significant loss in accuracy. The ranges represented by each bin can vary, such that at small coefficient ranges (e.g., representing small movements) the range of each bin can be relatively small. In contrast, a high movement ranges (e.g., the user making significant movements) the range of a bin may be greater because at high levels of movement the user is almost certainly awake.

The motion data processing system 214 can generate a series of sleep coefficients for a series of consecutive time intervals which may be referred to as a sleep log. For example, the motion data processing system 214 can generate sleep coefficients for 40 minutes of sequential time intervals and store it as a sleep log. Other lengths of time can be used. Each time interval in the sequence can be designated as including movement or not including movement based on their associated sleep coefficients (or based on the bin into which their associated sleep coefficients are sorted). The data in a sleep log can be used as input to a machine-learned model to determine whether the user is asleep during the period represented by the sleep log or not. However, if the machine-learned model has not been trained for a particular sleeper type, the output of the model can be inaccurate. As such, the user classification system 212 can determine a sleeper type for the user to ensure their sleep log data is accurately analyzed.

The sequence of time intervals can be transmitted to the sleeper type determination system 218. The sleeper type determination system 218 can determine the sleeper type of user based on the classification of each time interval in the sequence of time intervals of motion sensor data. The sleeper type determination system 218 can determine one or more factors based on the motion sensor data for the sleep session. The factors can include an average amount of time between movements during the sleep session, the minimum or average number of movements in any 100-minute period during the sleep session, and/or other indications of the amount, frequency, or duration of movement during sleep.

Based on the one or more sleep factors, the sleeper type determination system 218 can determine a sleeper type for the user. For example, if the number of instances of user movement during a period of sleep exceeds a particular threshold, the sleeper type determination system 218 can determine that the sleeper type of the user is a high-movement sleeper type (e.g., a twitchy sleeper type). Other potential sleeper types can be associated with sleep disorders (e.g., insomnia), be based on a user's sleep habits (e.g., a user who has several shorter sleep sessions rather than one long one), and so on. It should be noted that the sleeper type determination system 218 is described as primarily using previously collected sleep movement data to determine the sleeper type of the user. However, other data, such as demographic data, location data, ambient temperature data, and so on can be used as part of this determination as well.

The user classification system 212 can transmit the determined sleeper type to the sleep analysis system 220. In some examples, the user classification system 212 can store the determined sleeper type in memory 204 and the sleep analysis system 220 can access it as needed.

The sleep analysis system 220 can select a particular sleep analysis model for use when analyzing the sleep data of the user. For example, the sleep analysis system 220 can have access to a plurality of different computer-learned models, where each model has been trained based on data from or associated with a particular sleeper type. Thus, when the sleeper type of a user is determined, the sleep analysis system 220 can select a sleep analysis model that has been trained to analyze the motion sensor data or other sleep data produced by a user with that sleeper type during a sleep session.

Additionally, or alternatively, a single sleep analysis model is used but the specific parameter values associated with the model can be adjusted based on the sleeper type of a user. Thus, when a user's sleeper type is determined, the sleep analysis system 220 can select the particular parameters associated with the sleeper type and set the models parameters to the particular parameters during the analysis of sleep data associated with the user.

In addition or alternatively, in some examples, the sleep analysis model can include (or use as a post-processing system) one or more rule-based classification steps that can perform additional analysis of the sleep characteristic data generated by the sleep analysis model in one or more specific situations. In some examples, the rule-based classification steps can be altered based on the sleeper type of the user (e.g., such that they produce different sleep characteristics for users of a first sleeper type and users of a second sleeper type.) In this way, the sleep analysis system 220 can select the most appropriate tools to analyze the motion sensor data of the user based on the user's sleeper type.

Examples of the rule-based classification steps can include a post-processing rule that changes the classification of a user from asleep to awake for a particular time interval if the sleep coefficient for particular time intervals exceeds a predetermined threshold. However, if the user is determined to be a high-movement user, the value of the predetermined threshold can be raised or the entire post-processing rule can be disabled. In another example, a post-processing rule can change the classification for a sleep period from asleep to awake if a certain percentage of sleep intervals included therein have a sleep coefficient above a threshold. As with the first example, if the user is determined to be a high-movement type user, the threshold of the rule-based classification step can be raised or the rule itself can be suspended. As such, in addition to selecting a specific sleep analysis model based on the user's sleeper type, hard coded post processing rules can also be changed (e.g., thresholds adjusted) or suspended such that they are not applied to high movement sleeper type users.

Using motion sensor data detected from a user during a second period as input to the sleep analysis system 220 (e.g., different from the data for the first period that was used to determine the sleeper type of the user), the sleep analysis system 220 can determine one or more sleep characteristics for the second period. For example, the first set of sleep data can be past sleep data for a user (e.g., data from a plurality of sleep sessions), while the second set of sleep data can be data generated by a sensor during a most recent sleep session for a user.

In some examples, the sleep analysis system 220 can determine whether the user was asleep during one or more portions of the second period. If so, the sleep analysis system 220 can determine when the sleep session began and when it ended. In addition, the sleep analysis system 220 can determine one or more sleep states for a user during the sleep session, the amount of time spent in each sleep state, and the time at which the user transitioned from one sleep state to another sleep state. Sleep states can include an REM sleep state, a light sleep state, and a deep sleep state. In some examples, other sleep characteristics can be determined based on the sleep analysis model. For example, the sleep analysis model can generate a sleep score, representing the overall quality of the sleep session (e.g., based on a length of the sleep session and the time spent in each sleep state). Additional parameters that are not specifically related to sleep can use the data from the sleep analysis model as one factor used in their analysis such as a stress score and/or a fitness readiness score.

Once one or more sleep have been generated, the sleep analysis system 220 can provide one or more sleep parameters to the display system 222. The display system 222 can present one or more sleep parameters to the user via a display included in the wearable computing device 100. In some examples, a user can request, via an interface with the wearable computing device 100, that the device display one or more sleep parameters. The wearable computing device 100 can present the sleep parameters to the user (e.g., amount of sleep, quality of sleep, time of sleep sessions, and so on).

Figure 3:
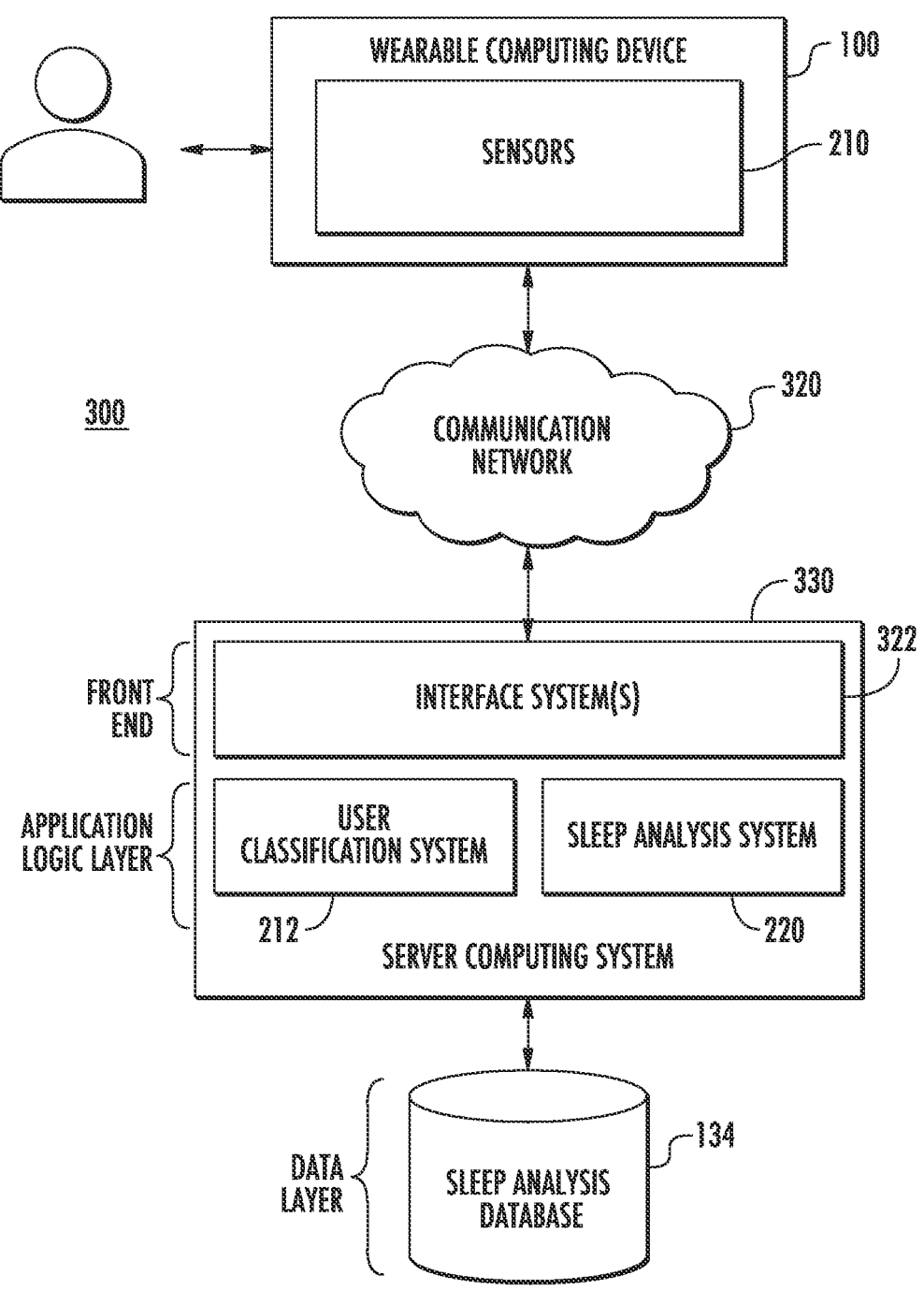
FIG. 3 illustrates a block diagram of a computing environment including a wearable computing device connected to a server computing system via a network in accordance with example embodiments of the present disclosure.

FIG. 3 depicts an example client-server environment according to example embodiments of the present disclosure. The client-server system environment 300 includes one or more wearable computing devices 100 and a server computing system 330. One or more communication networks 320 can interconnect these components. The communication networks 320 may be any of a variety of network types, including local area networks (LANs), wide area networks (WANs), wireless networks, wired networks, the Internet, personal area networks (PANs), or a combination of such networks.

A wearable computing device 100 can include, but is not limited to, smartwatches, fitness bands, computing devices integrated into jewelry such as smart rings or smart necklaces, computing devices integrated into items of clothing such as jackets, shoes, and pants, and wearable glasses with computing elements included therein. In some examples, a wearable computing device 100 can include one or more sensors intended to gather information with the permission of the user that is wearing the wearable computing device. In some examples, the wearable computing device 100 can connect to another computing device, such as a personal computer (PC), a laptop, a smartphone, a tablet, a mobile phone, an electrical component of a vehicle, or any other electronic device capable of communication with the communication network 320. A wearable computing device 100 can include one or more user application(s) such as search applications, communication applications, navigation applications, productivity applications, game applications, word processing applications, or any other applications. The user application(s) can include a web browser. The wearable computing device 100 can use a web browser (or other application) to send and receive requests to and from the server computing system 330.

In some examples, the wearable computing device 100 can include one or more sensors that can be used to determine the movement of a user at a particular time. For example, the sensors 210 can include, but are not limited to, motion sensors (e.g., accelerometer), a pulse oximeter, an IR motion sensor, skin temperature sensors, internal device temperature sensors, location sensors (e.g., GPS),), altitude sensors, heart rate sensors, audio sensors, pressure sensors, and other physiological sensors.

As shown in FIG. 3, the server computing system 330 can generally be based on a three-tiered architecture, consisting of a front-end layer, application logic layer, and data layer. As is understood by skilled artisans in the relevant computer and Internet-related arts, each component shown in FIG. 3 can represent a set of executable software instructions and the corresponding hardware (e.g., memory and processor) for executing the instructions. To avoid unnecessary detail, various components and engines that are not germane to conveying an understanding of the various examples have been omitted from FIG. 3. However, a skilled artisan will readily recognize that various additional components and engines may be used with a server computing system 330, such as that illustrated in FIG. 3, to facilitate additional functionality that is not specifically described herein. Furthermore, the various components depicted in FIG. 3 may reside on a single server computer or may be distributed across several server computers in various arrangements. Moreover, although the server computing system 330 is depicted in FIG. 3 as having a three-tiered architecture, the various example embodiments are by no means limited to this architecture.

As shown in FIG. 3, the front end can consist of an interface system(s) 322, which receives communications from one or more wearable computing devices 100 and communicates appropriate responses to the wearable computing devices 100. For example, the interface system(s) 322 may receive requests in the form of Hypertext Transfer Protocol (HTTP) requests, or other web-based, application programming interface (API) requests. The wearable computing devices 100 may be executing conventional web browser applications or applications that have been developed for a specific platform to include any of a wide variety of mobile devices and operating systems.

As shown in FIG. 3, the data layer can include a sleep analysis database 134. In some example embodiments, the sleep analysis database 134 can store a variety of data including, but not limited, data associated with a plurality of sleep analysis models (e.g., one or more sleep analysis models for each sleeper type). The sleep analysis database 134 can include sleep and motion data received from the wearable computing device 100 and representing data gathered by the one or more sensors 210 included in the wearable computing device 100. The sleep analysis database 134 can also include data generated by the user classification system 212, such as a movement classification for one or more time intervals (e.g., a classification of whether a particular time interval includes user movement or not). The sleep analysis database 134 can also include information generated by the sleep analysis system 220 including a determination whether the user was asleep at a particular time, the length and quality of a user's sleep, and so on.

The application logic layer can include application data that can provide a broad range of other applications and services that allow users to access or receive geographic data for navigation or other purposes. The application logic layer can include a user classification system 212 and a sleep analysis system 220.

The user classification system 212 can receive via the information interface system 322, motion data from the sensors 210 included in the wearable computing device 100. The user classification system 212 can analyze the motion data to determine for each interval of a plurality of time intervals whether the user was moving during that time interval. In some examples, the user classification system 212 can generate one or more sleep factors based on the motion data and information of whether the user was moving in each of the plurality of time intervals. Based on the one or more sleep factors, the user classification system 212 can identify the sleeper type associated with the user.

The sleep analysis system 220 can be used once the sleeper type of a user has been identified to select a particular sleep analysis model for use when analyzing the sleep data of the user. For example, the sleep analysis system 220 can have access to a plurality of different computer-learned models (e.g., in sleep analysis database 134), where each model has been trained based on data from or associated with a particular sleeper type. Thus, when the sleeper type of a user is determined, the sleep analysis system 220 can select a sleep analysis model that has been trained to more accurately analyze the motion sensor data or other sleep data produced by a user with that sleeper type during a sleep period.

Once the sleep analysis model has been selected, the sleep analysis system 220 can receive further motion data from a sensor 210 included in the wearable computing device 100. Using this detected motion sensor data as input to the sleep analysis model (e.g., different from the data for the first period that was used to determine the sleeper type of the user), the sleep analysis system 220 can determine one or more sleep characteristics for the second period. In some examples, the sleep analysis system 220 can determine whether the user was asleep during the second period. If so, the sleep analysis system 220 can determine when the sleep session began and when it ended.

In addition, the sleep analysis system 220 can determine a current sleep state for the user. Sleep states can include a REM sleep state, a light sleep state, and a deep sleep state. In some examples, other sleep characteristics can be determined based on the sleep analysis model. For example, the sleep analysis model can generate a sleep score, representing the overall quality of the sleep session (e.g., based on a length of the sleep session and the time spent in each sleep state). Additional characteristics that are not specifically related to sleep can be determined such as a stress score and/or a fitness readiness score. The one or more sleep characteristics can be transmitted to the wearable computing device 100 for display to a user.

By sending sensor data captured at a particular wearable computing device 100 to a server system for analysis, the wearable computing device 100 can minimize the amount of memory and power used at the wearable computing device 100 while still receiving sleep characteristics determined by a machine-learned model using a significant number of resources. By centralizing the analysis of sleep data to a server system, the user experience is improved while the cost of the wearable computing device 100 is minimized.

Figure 4:
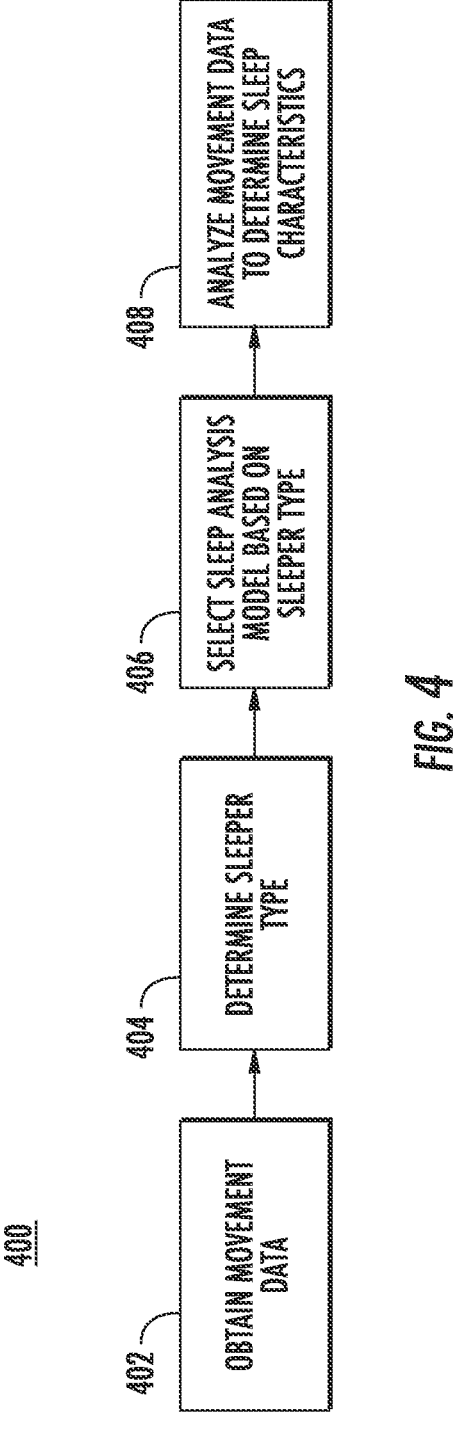
FIG. 4 is a block diagram of an example process for determining a sleeper type for a user in accordance with example embodiments of the present disclosure.

FIG. 4 is a block diagram 400 of an example process for determining a sleeper type for a user in accordance with example embodiments of the present disclosure. In this example, a user classification system (e.g., user classification system 212 in FIG. 2) can obtain, at 402, previously detected motion data for a user. For example, the user classification system can access stored historical motion data for the user including at least one sleep session or suspected sleep session.

The previously detected motion data can include motion data generated by the motion sensor (e.g., sensor 210 in FIG. 2). In some examples, the motion sensor is an accelerometer, and the motion data is represented as a range of motion along three axes (x, y, and z axes) during the period in which the data was gathered. For example, the accelerometer can measure acceleration in three dimensions and associate the measured acceleration with specific timestamps (or another method of determining when specific movements occurred). In some examples, the user classification system 212 can divide the motion data into one or more time intervals. For example, each time interval can represent 30 seconds. Other lengths of time can be used for the time intervals. The user classification system 212 can generate a classification for each respective time interval, the classification indicating whether the user is detected as moving during that respective time interval.

Once the user motion data has been analyzed, the user classification system 212 can determine, at 404, the sleeper type for the user based on the analysis of the motion data. In some examples, the sleeper type can be a high movement sleeper type. In the specific example of the high movement sleeper type, the determination can be based on the number of times a user moves in a particular interval (e.g., within an hour). In the specific example of the high movement user type, the number of times a user moves within a particular interval can be compared against a threshold value. If the number of movements during the respective interval exceeds the threshold, the user classification system 212 can determine that the user is a high movement sleeper type user.

Once the sleeper type has been determined for a respective user, the sleep analysis system 220 can select, at 406, a sleep analysis model based on that sleeper type. Thus, the sleep analysis model used to analyze, at 408, the motion data of a high movement sleeper type user will be different than the sleep analysis model selected for a user that is not a high movement sleeper type user. This allows the sleep analysis model to accurately determine the sleep characteristics of a user when otherwise it would be difficult based on the user's sleeper type. For example, if a sleep analysis model trained for a user with a sleeper type other than a high-movement sleeper type was used to analyze the motion data of a high movement user, the sleep analysis model might not detect sleep at all from the high movement user during an entire sleep session.

The sleep analysis system 220 can determine, using the selected sleep analysis model, one or more sleep characteristics of the user. For example, the sleep characteristics can include a determination of whether the user is asleep at a particular point in time, the start and stop of a sleep session, the specific sleep state a user is in, and so on.

Figure 5:
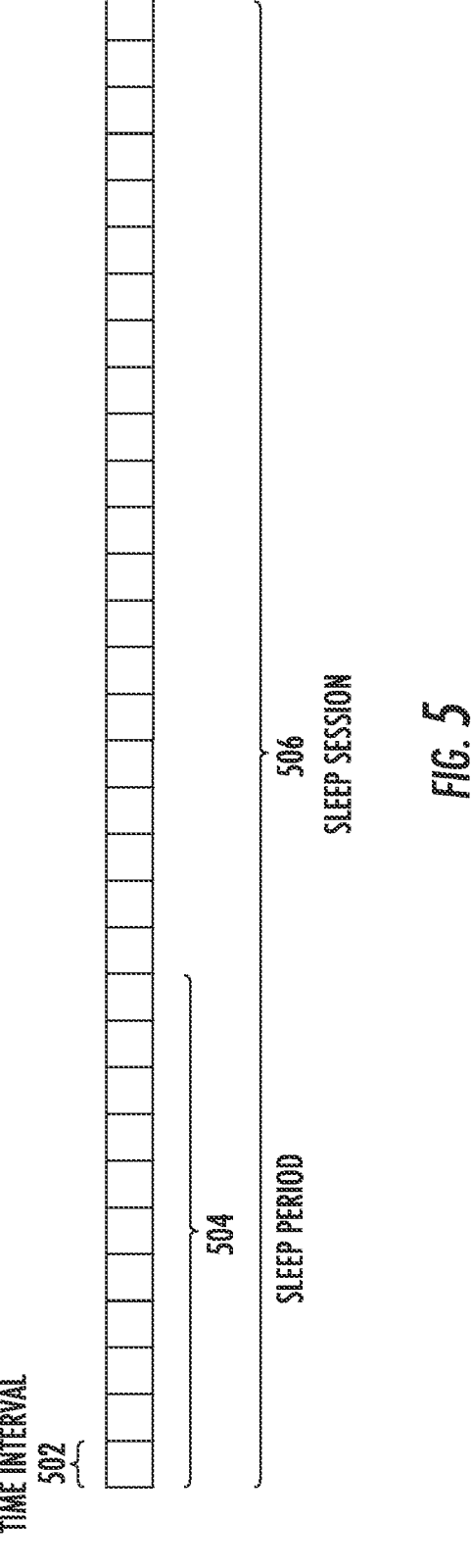
FIG. 5 illustrates an example time series motion data in accordance with example embodiments of the present disclosure.

FIG. 5 illustrates an example of time series motion data in accordance with example embodiments of the present disclosure. In this example, an entire sleep session 506 can be divided into a plurality of time intervals 502. Each respective interval in the plurality of time intervals 502, can be classified (based on sensor data captured during the time represented by the respective time interval) based on a sleep coefficient for each interval The sleep coefficient can be generated based on a range of movement detected by an accelerometer during the time interval 502. If the range of movement exceeds a threshold, the time interval 502 can be associated with a movement by the user. If the range of movement does not exceed a threshold, the time interval 502 can be associated with no movement.

In some examples, the one or more time intervals 502 can be grouped into a sleep period 504. A sleep period 504 can refer to a group of time intervals 502 that together comprise an amount of time that is less than the entire sleep session 506 but more than a single time interval 502. In some examples, a sleep period 504 can represent a period of sleep during a sleep session 506 separated by one or more periods of movement.

Figure 6:
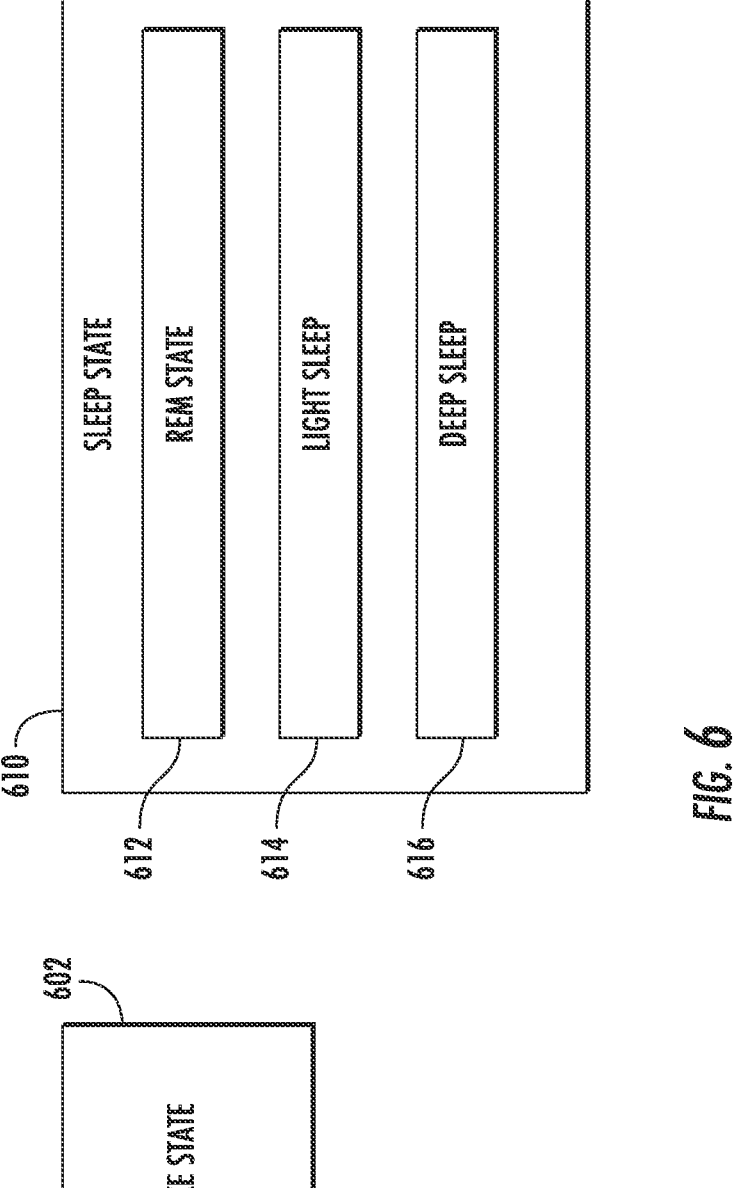
FIG. 6 illustrates a representation of possible sleep states in accordance with example embodiments of the present disclosure.

FIG. 6 illustrates a representation of possible sleep states in accordance with example embodiments of the present disclosure. For example, one possible state is the awake state 602 in which the user is determined not to be asleep. In some examples, the awake state 602 can be identified based on a plurality of activity metrics including the user interacting with the wearable computing device or based on an amount of movement detected from a user exceeding a predetermined threshold for movement.

In some examples, the sleep state 610 can include one or more distinct states such as a REM state 612 that is characterized by the rapid movement of the eyes and low muscle tone (e.g., residual muscle tension) in the body. Another state of sleep can be a light sleep state 614 that can be characterized by muscle relaxation, cessation of eye movements, reduced breathing rate and heart rate, lower body temperature, and slower brain waves. During the light sleep state 614 a user may be awoken relatively easily.

A third state of sleep can be a deep sleep state 616. The deep sleep state 616 can be characterized by further relaxation of the muscles, breathing and heart rate lower than the light sleep state, further slowing of brain waves, and difficulty in waking the user from sleep.

Figure 7:
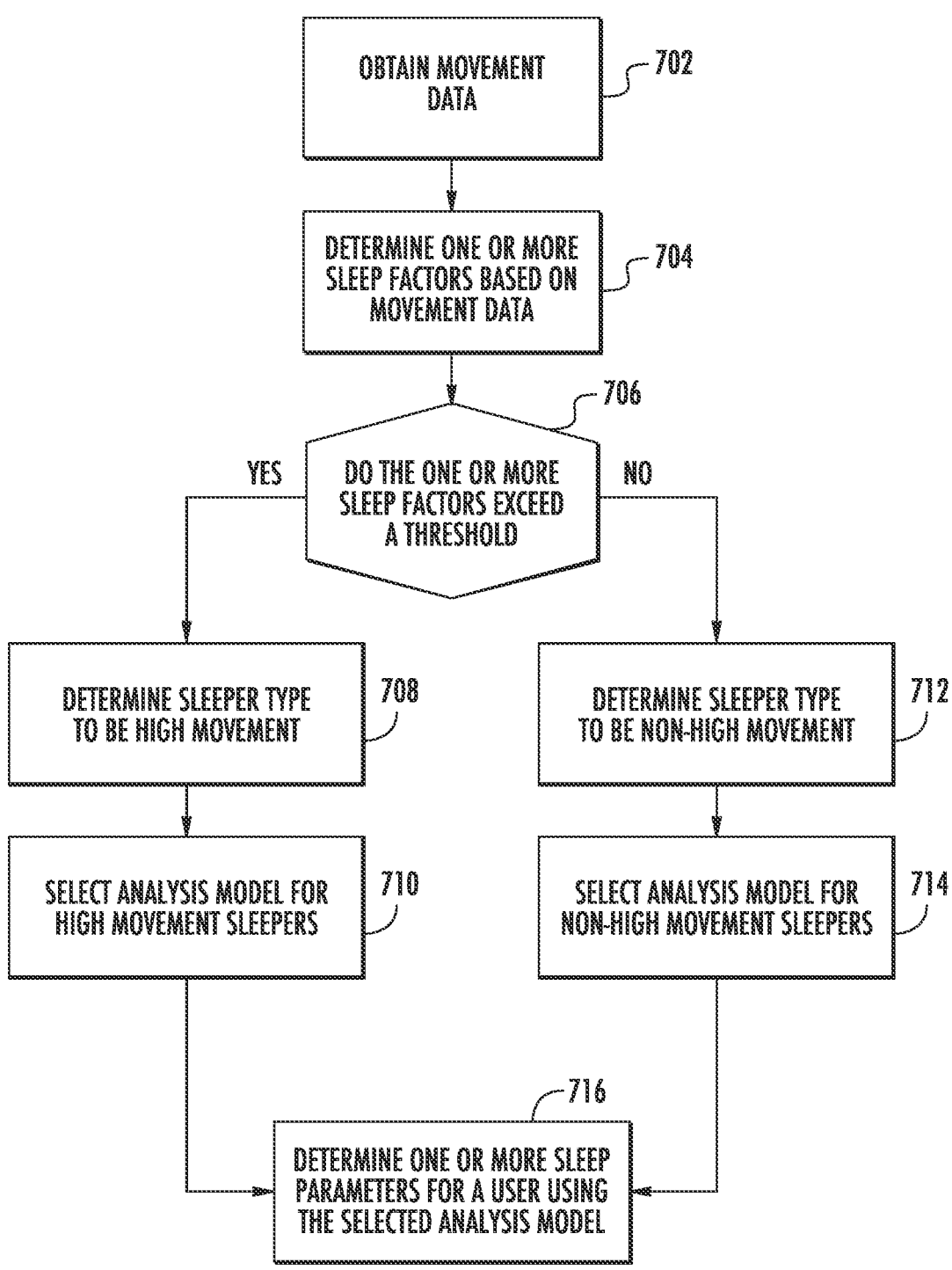
FIG. 7 illustrates an example process for determining a sleeper type for a user in accordance with example embodiments of the present disclosure.

FIG. 7 illustrates an example process for determining a sleeper type for a user in accordance with example embodiments of the present disclosure. In some examples, a user classification system (e.g., user classification system 212 in FIG. 2) can obtain, at 702, motion data for a user during a period of time. In some examples, the period of time can be a period in which the user classification system 212 determines that the user has slept.

The user classification system 212 can analyze the motion data to determine, at 704, one or more sleep factors. For example, the motion data can be analyzed to determine when during the motion data the user was asleep and when the user was awake. The user classification system 212 can determine each time a user moved during a period of sleep. As noted above, the movement of user can be determined based on a variety of different sensors including an accelerometer to measure the movement of the user, an infrared sensing system to detect the movement of a user in a space, a heartbeat monitor to determine user activity based on their heartbeat, and any other sensor that is capable of estimating a user's movement based on signals obtained from a user.

In some examples, the sleeper type determination system can determine, at 704, one or more sleep factors based on the motion data. The sleep factors can be any measure of the quality duration of a user to sleep that is useful for determining a user sleeper type. A specific example can include the number of times a user moves during an hour of sleep. In some examples, the number of times a user moves per hour can be averaged over an entire sleep session. Another factor can include the average length of time between movements. In addition to the two specific examples given here, a variety of other measurements can be used as sleep factors when evaluating a user sleeper type. For example, any data that is an indication of the amount, frequency, or duration of movement during sleep, can be used as potential sleep factors.

In some examples, the one or more sleep factors can be used as input to a classification system that can determine a user sleeper type based on multiple inputs. The one or more sleep factors can be used directly or can be used to generate a sleep factor score based on the motion data. The user classification system 212 can determine, at 706, whether the one or more sleep factors (or the sleep factor score) exceeds a threshold. The threshold can be a predetermined value that can be used to separate one sleeper type from another sleeper type. If the one or more sleep factors (or sleep factor score) exceeds the threshold, the user classification system can determine, at 708, that the user sleeper type is a high movement sleeper type. Based on that determination, a user classification system 212 can select, at 710, a sleep analysis model associated with high movement sleeper type users.

In accordance with the determination that the sleep factors (or sleep score) do not exceed the threshold, the user classification system 212 can determine, at 712, that the user is not a high movement sleeper type user. The user classification system 212 can select, at 714, a sleep analysis model that is associated with users who are not determined to be high movement sleeper type users.

Once a sleep analysis model has been selected, a sleep analysis system 220 can use the selected sleep analysis model to determine, at 716, sleep parameters based on motion data captured by one or more sensors.

Figure 8:
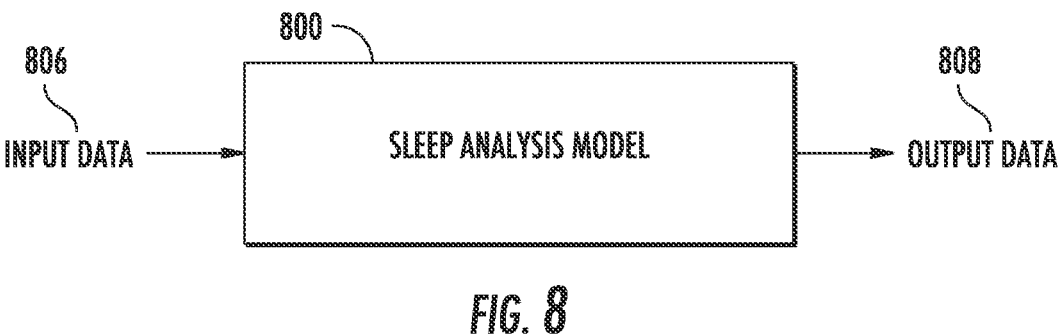
FIG. 8 depicts a block diagram of an example gesture classification machine-learned model according to example embodiments of the present disclosure.

FIG. 8 depicts a block diagram of an example sleep analysis model according to example embodiments of the present disclosure. A machine-learned sleep analysis model 800 can take motion data from a user as input data 806. For example, the sleep analysis model 800 can generate one or more sleep parameters based on the input motion data. Once trained, the machine-learned sleep analysis model can output 808 one or more sleep factors such as a determination whether the user is asleep during a particular period represented by the input motion data.

In some examples, the machine-learned sleeper analysis model 800 can otherwise include various machine-learned models such as neural networks (e.g., deep neural networks), other types of machine-learned models, including non-linear models, and/or linear models, or binary classifiers. Neural networks can include feed-forward neural networks, recurrent neural networks (e.g., long short-term memory recurrent neural networks), convolutional neural networks, or other forms of neural networks.

A variety of training techniques can be used to train the machine-learned sleep analysis model 800. Specifically, the machine-learned sleep analysis model 800 can be trained using one of a plurality of semi-supervised training techniques. The machine-learned sleep analysis model 800 can also be trained using a supervised training technique, such as, for example, backward propagation of errors. For example, a loss function can be back-propagated through the model(s) to update one or more parameters of the model(s) (e.g., based on a gradient of the loss function). Various loss functions can be used such as mean squared error, likelihood loss, cross entropy loss, hinge loss, and/or various other loss functions. Gradient descent techniques can be used to iteratively update the parameters over several training iterations. In some implementations, performing backward propagation of errors can include performing truncated backpropagation through time. Generalization techniques (e.g., weight decays, dropouts, etc.) can be performed to improve the generalization capability of the models being trained.

Figure 9:
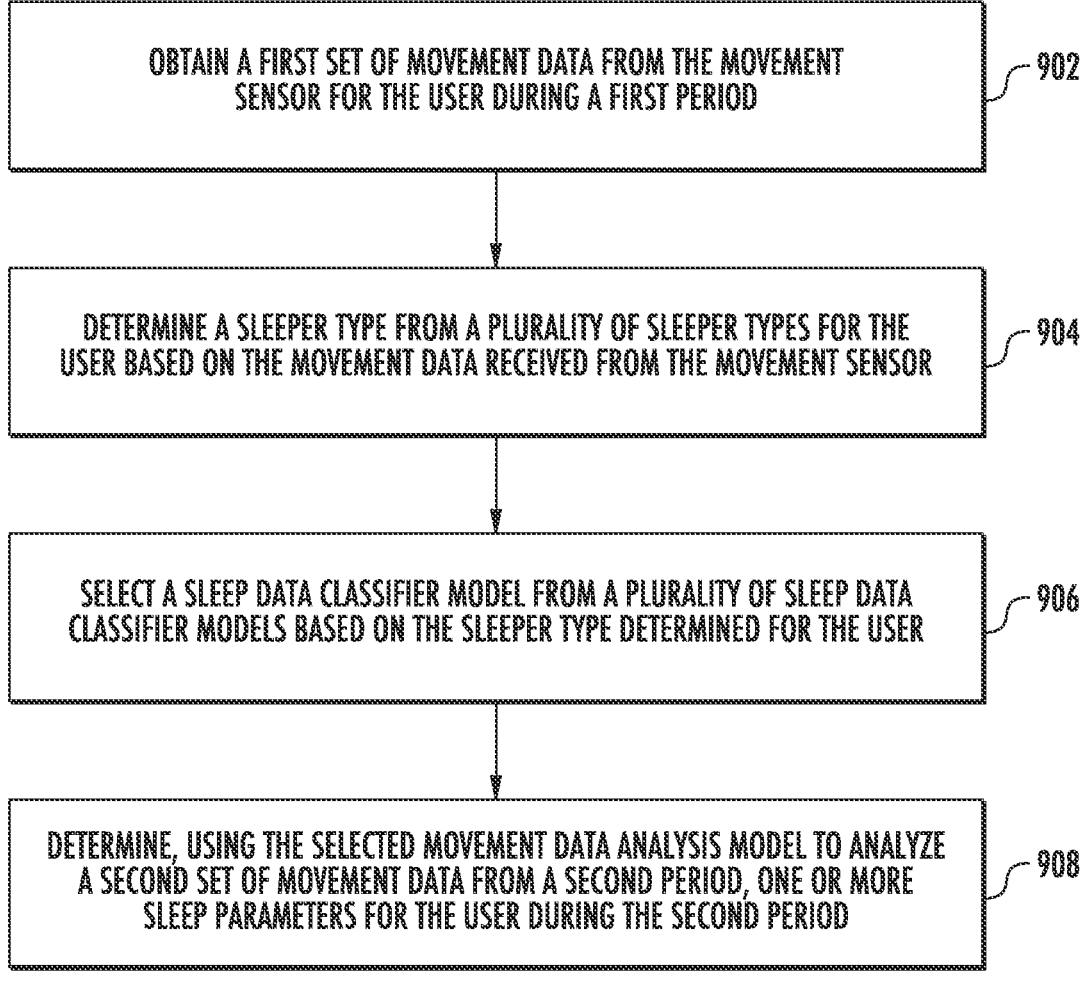
FIG. 9 is a flowchart depicting an example process of determining a sleeper type of a user based on motion data in accordance with example embodiments of the present disclosure.

FIG. 9 is a flowchart depicting an example process of determining a sleeper type of a user based on motion data in accordance with example embodiments of the present disclosure. In some examples, a wearable computing device (e.g., a fitness band or smartwatch) 100 can include a motion sensor configured to generate motion sensor data based on the movements of a user. The motion sensor can be an accelerometer. The accelerometer can measure movement (or acceleration) in each of the three axes. The wearable computing device can include a user classification system (e.g., user classification system 212 in FIG. 2) and a sleep analysis system (e.g., sleep analysis system 220 in FIG. 2). The user classification system 212 can obtain, at 902, a first set of motion sensor data from the motion sensor for the user during a first period. In some examples, the first period includes one or more sleep sessions.

The user classification system 212 can determine sleep coefficient data based on a range of movement detected by the accelerometer during one or more time intervals. The user classification system 212 can classify the user as either moving or still during each respective time interval in the one or more time intervals.

The user classification system 212 can determine, at 904, a sleeper type from a plurality of sleeper types for the user based on the motion sensor data received from the motion sensor. In some examples, the plurality of sleeper types can include a high-movement sleeper type. The user classification system 212 can determine a sleeper type for the user based on the motion sensor data received from the motion sensor by determining an average number of user movements during the first period. The user classification system 212 can determine that the average number of user movements by the user during the first period exceeds a high movement threshold. The user classification system 212 can, in response to determining that the average number of user movements by the user during the first period exceeds a high movement threshold, determine that the sleeper type for the user is the high-movement sleeper type.

The user classification system 212 can determine a sleeper type for the user based on the motion sensor data received from the motion sensor by determining an average amount of time between time intervals in the one or more time intervals in which the user is classified as moving. The user classification system 212 can determine that the average amount of time between time intervals in the one or more time intervals in which the user is classified as moving exceeds a high movement threshold. In response to determining that the average amount of time between time intervals in the one or more time intervals in which the user is classified as moving exceeds a high movement threshold, the user classification system 212 can determine that the sleeper type for the user is the high-movement sleeper type.

The user classification system 212 can select, at 906, a sleep analysis model from a plurality of sleep analysis models based on the sleeper type determined for the user. In some examples, the plurality of sleep analysis models can be machine-learned models. In some examples, each sleep analysis model in the plurality of sleep analysis models is trained to accurately analyze data from a different sleeper type in the plurality of sleeper types. In some examples, the sleep analysis model includes one or more post-processing rules.

In some examples, the sleep analysis system 220 can, at 908, use the selected sleep analysis model to analyze a second set of motion sensor data from a second period to determine one or more sleep characteristics for the user during the second period. In some examples, the one or more sleep characteristics include data indicating whether the user was asleep during the second period. In some examples, the one or more sleep characteristics include data indicating a sleep state of the user during the second period. In some examples, the one or more sleep characteristics include data indicating a length of a sleep session.

The technology discussed herein refers to servers, databases, software applications, and other computer-based systems, as well as actions taken and information sent to and from such systems. One of ordinary skill in the art will recognize that the inherent flexibility of computer-based systems allows for a great variety of possible configurations, combinations, and divisions of tasks and functionality between and among components. For instance, server processes discussed herein may be implemented using a single server or multiple servers working in combination. Databases and applications may be implemented on a single system or distributed across multiple systems. Distributed components may operate sequentially or in parallel.

While the present subject matter has been described in detail with respect to specific example embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations, and/or additions to the present subject matter as would be readily apparent to one of ordinary skill in the art.

What is claimed is:

1. A wearable computing device, comprising:
   a motion sensor configured to generate motion sensor data based on movements of a user, wherein the motion sensor is worn on a wrist of the user; and
   one or more processors that execute computer-readable instructions to:

obtain a first set of motion sensor data from the motion sensor for the user during a first period;

determine a sleeper type from a plurality of sleeper types for the user based on the first set of motion sensor data received from the motion sensor, wherein the plurality of sleeper types include a high-movement sleeper type and wherein determining the sleeper type from the plurality of sleeper types for the user based on the first set of motion sensor data received from the motion sensor comprises:

determining an average number of user movements during the first period;

determining that the average number of user movements by the user during the first period exceeds a high movement threshold; and in response to determining that the average number of user movements by the user during the first period exceeds a high movement threshold, determining that the sleeper type for the user is the high-movement sleeper type;

select a respective machine-learned sleep analysis model from a plurality of machine-learned sleep analysis models based on the sleeper type determined for the user, wherein the respective machine-learned model has been trained using previously captured data from users of the determined sleeper type; and use the respective machine-learned sleep analysis model to analyze a second set of motion sensor data from a second period to determine one or more sleep characteristics for the user during the second period.

2. The wearable computing device of claim 1, wherein the first period includes one or more sleep sessions.

3. The wearable computing device of claim 1, wherein the motion sensor is an accelerometer.

4. The wearable computing device of claim 3, wherein the one or more processors determine a sleeper type from a plurality of sleeper types for the user based on the first set of motion sensor data received from the motion sensor by: generating sleep coefficient data based on a range of movement detected by the accelerometer during in the first set of motion sensor data.

5. The wearable computing device of claim 4, wherein the one or more processors:

classify the user as either moving or still during each respective time interval in the one or more time intervals.

6. The wearable computing device of claim 5, wherein the one or more processors determine a sleeper type for the user based on the first set of motion sensor data received from the motion sensor by:

determining an average amount of time between time intervals in which the user is classified as moving;

determining that the average amount of time between time intervals in which the user is classified as moving is below a high movement threshold; and in response to determining that the average amount of time between time intervals in which the user is classified as moving is below a high movement threshold, determining that the sleeper type for the user is the high-movement sleeper type.

7. The wearable computing device of claim 1, wherein each sleep analysis model in the plurality of sleep analysis models is trained to analyze data from a different sleeper type in the plurality of sleeper types.

8. The wearable computing device of claim 1, wherein the respective sleep analysis model includes one or more post-processing rules.

9. The wearable computing device of claim 1, wherein the one or more sleep characteristics include data indicating whether the user was asleep during the second period.

10. The wearable computing device of claim 1, wherein the one or more sleep characteristics include data indicating a sleep state of the user during the second period.

11. The wearable computing device of claim 1, wherein the one or more sleep characteristics include data indicating a length of a sleep session.

12. A computer-implemented method, the method comprising:

obtaining, by a computing device including one or more processors, a first set of motion sensor data from the motion sensor for a user during a first period, wherein the motion sensor is worn on a wrist of the user;

determining, by the computing device, a sleeper type from a plurality of sleeper types for the user based on the first set of motion sensor data received from the motion sensor, wherein the plurality of sleeper types include a high-movement sleeper type and wherein determining the sleeper type from the plurality of sleeper types for the user based on the first set of motion sensor data received from the motion sensor comprises:

determining, by the computing device, an average number of user movements during the first period;

determining, by the computing device, that the average number of user movements by the user during the first period exceeds a high movement threshold; and in response to determining that the average number of user movements by the user during the first period exceeds a high movement threshold, determining, by the computing device, that the sleeper type for the user is the high-movement sleeper type;

select, by the computing device, a respective machine-learned sleep analysis model from a plurality of machine-learned sleep analysis models based on the sleeper type determined for the user, wherein the respective machine-learned model has been trained using previously captured data from users of the determined sleeper type; and use, by the computing device, the respective machine-learned sleep analysis model to analyze a second set of motion sensor data from a second period to determine one or more sleep characteristics for the user during the second period.

13. The computer-implemented method of claim 12, wherein the first period includes one or more sleep sessions.

14. The computer-implemented method of claim 12, wherein the motion sensor is an accelerometer.

15. The computer-implemented method of claim 14, further comprising:

generating, by the computing devices, sleep coefficient data based on a range of movement detected by the accelerometer during one or more time intervals.

16. A non-transitory computer readable storage medium having computer-readable program instructions embodied thereon that, when executed by one or more processors, cause the one or more processors to:

obtain a first set of motion sensor data from the motion sensor for a user during a first period, wherein the motion sensor is worn on a wrist of the user;

determine a sleeper type from a plurality of sleeper types for the user based on the first set of motion sensor data received from the motion sensor, wherein the plurality of sleeper types include a high-movement sleeper type and wherein determining the sleeper type from the plurality of sleeper types for the user based on the first set of motion sensor data received from the motion sensor comprises:

determining an average number of user movements during the first period;

determining that the average number of user movements by the user during the first period exceeds a high movement threshold; and in response to determining that the average number of user movements by the user during the first period exceeds a high movement threshold, determining that the sleeper type for the user is the high-movement sleeper type;

select a respective machine-learned sleep analysis model from a plurality of machine-learned sleep analysis models based on the sleeper type determined for the user, wherein the respective machine-learned model has been trained using previously captured data from users of the determined sleeper type; and use the respective machine-learned sleep analysis model to analyze a second set of motion sensor data from a second period to determine one or more sleep characteristics for the user during the second period.

* * * * *